(12) United States Patent  
Dea

(10) Patent No.: US 8,739,800 B2  
(45) Date of Patent: Jun. 3, 2014

(54) NON-CONTACT ELECTRONIC TOOL FOR QI EMISSION AND AMPLIFICATION

(76) Inventor: Jack Y Dea, San Diego, CA (US)

(*) Notice: Subject to any disclaimer, the term of this patent is extended or adjusted under 35 U.S.C. 154(b) by 138 days.

(21) Appl. No.: 13/546,812

(22) Filed: Jul. 11, 2012

(65) Prior Publication Data

US 2013/0012759 A1      Jan. 10, 2013

Related U.S. Application Data

(63) Continuation-in-part of application No. 13/176,505, filed on Jul. 5, 2011.

(51) Int. Cl.
*A61B 19/00*      (2006.01)

(52) U.S. Cl.
USPC ............................................. 128/897

(58) Field of Classification Search
CPC ............ A61N 2/02; A61N 2/008; A61N 1/40
USPC ................. 600/1, 9, 13, 15; 606/33; 128/897; 607/100
See application file for complete search history.

(56) References Cited

U.S. PATENT DOCUMENTS

| | | | |
|---|---|---|---|
| 5,057,095 A | | 10/1991 | Fabian |
| 6,132,357 A | * | 10/2000 | Sabuda ............................ 600/1 |
| 7,257,967 B2 | | 8/2007 | Rheinstein |
| 7,613,523 B2 | | 11/2009 | Eggers et al. |
| 7,988,613 B2 | | 8/2011 | Becker |
| 2005/0081561 A1 | | 4/2005 | Eggleston |
| 2007/0234757 A1 | | 10/2007 | Sherman |
| 2009/0100866 A1 | | 4/2009 | Creel |
| 2010/0130945 A1 | | 5/2010 | Laniado et al. |

* cited by examiner

*Primary Examiner* — Jacqueline Cheng  
*Assistant Examiner* — Eileen Foley  
(74) *Attorney, Agent, or Firm* — Excelsior Patent Group; Bruce Hare

(57) ABSTRACT

This invention pertains to a non-contact Qi emission and amplification electronic device. Qi is a Chinese word for the life energy that circulates in human beings. The device is a passive electronic device, that is, it is not powered by any battery or electrical supply. It does not come into contact with the user. The user places the device a few feet away. As such the device is totally safe in terms of dangerous electrical shocks or electromagnetic emissions. The device has a switch to turn it on or off. The switch connects together electronic components, including a piezo-crystal, inside the device. Ambient fluctuations in the voltage of the piezo-crystal may produce an influence field that is broadcasted to an approximately six foot radius surrounding the device. The influence field feels like a cool breeze and affects the user in similar ways to the emitted Qi from Qi Gong practitioners.

9 Claims, 3 Drawing Sheets

NON-CONTACT ELECTRONIC TOOL FOR QI EMISSION AND AMPLIFICATION

CROSS-REFERENCE TO RELATED APPLICATIONS

This application is a continuation-in-part of U.S. patent application having Ser. No. 13/176,505, filed on Jul. 5, 2011.

FIELD OF THE INVENTION

The present invention relates to the technology of non-contact Qi emission and amplification using electronic components. Qi is the Chinese name for the life energy that circulates in the human body. Qi flows freely in a healthy body but is stagnant when the body becomes unhealthy. The invention uses an iron core driven by the voltage fluctuations of a piezo-crystal. No battery or power source is used. An influence field of around six feet surrounds the device. A person within the influence field will experience a subtle cool breeze which is the Qi field.

SUMMARY OF THE INVENTION

The field of Qi emission almost always involves a human emitter, usually a Qi Gong practitioner or a Qi Gong master. There is an obvious drawback in that a Qi Gong practitioner is not always available. For minor aches and pain, calling on a Qi Gong practitioner may not be worth the trouble and expense. Often times a person wants to have an energy boost every morning and it is impractical to call upon a Qi Gong practitioner every morning.

Originally, the inventor was developing devices that are able to simulate low frequency fields that often are observed preceding the occurrence of large earthquakes. The magnetic fields were produced from large coils. The electric fields were produced by a large iron ring core with toroidal windings. It was found that a quartz tuning crystal connected to the wiring of the toroid was able to emit a cool breeze. Refining the device to a passive device consisting of iron core, toroidal winded wiring, on-off switch, and quartz crystal, the device is able to generate a field that is very soothing, cooling, and feels similar to the Qi field emitted by Qi Gong practitioners.

One embodiment of the Qi emitter device is capable of producing an influence field of around six feet from the device. That is, the influence field of the device placed in the center of a twelve foot by twelve foot room will influence everybody in the room. One embodiment of the device is composed of a twenty-three inch by eighteen inch rectangular iron core, wiring, and a quartz crystal. Another embodiment of the device uses a two foot diameter iron ring core. A larger iron core may be used to generate a stronger influence field.

BRIEF DESCRIPTION OF THE DRAWINGS

The novel features of the invention are set forth in the appended claims. However, for purpose of explanation, several embodiments of the invention are set forth in the following drawings.

DETAILED DESCRIPTION

This invention pertains to a non-contact device that emits an influence field that is cool and soothing and acts similar to the Qi filed emitted by Qi Gong practitioners. The device may include an iron (or other ferro-magnetic) core, wiring and a piezo-crystal. The core may typically be an iron ring with a diameter of one to two feet. Square and rectangular (and/or otherwise-shaped) cores may be used.

Figure 1:
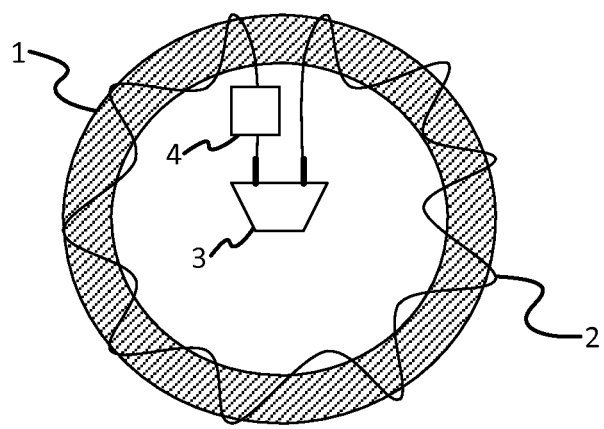
FIG. 1 shows an embodiment of the Qi emitter device with a round iron core.

FIG. 1 shows parts and connections of some embodiments of the invention. The iron core 1 may be wrapped in a toroidal fashion by a wire 2. Typically, one turn of wire may be winded per inch of core. However, the number of turns of wire is not critical. A piezo-crystal 3 with two conducting surfaces and two leads, is connected to the wire 2 (e.g., by soldering). A quartz crystal may typically be used as the piezo-crystal. An on-off, DPDT switch 4 may connect the wire 2 to one lead of the crystal 3. In the "off" position, the circuit is open. In the "on" position, the circuit is closed.

The quartz crystal 3 can be obtained from electronic supply sources. The wire 2 and on-off switch 4 can also be obtained from electronic supply sources. The iron core 1 can be obtained from specialty metal shops.

Figure 2:
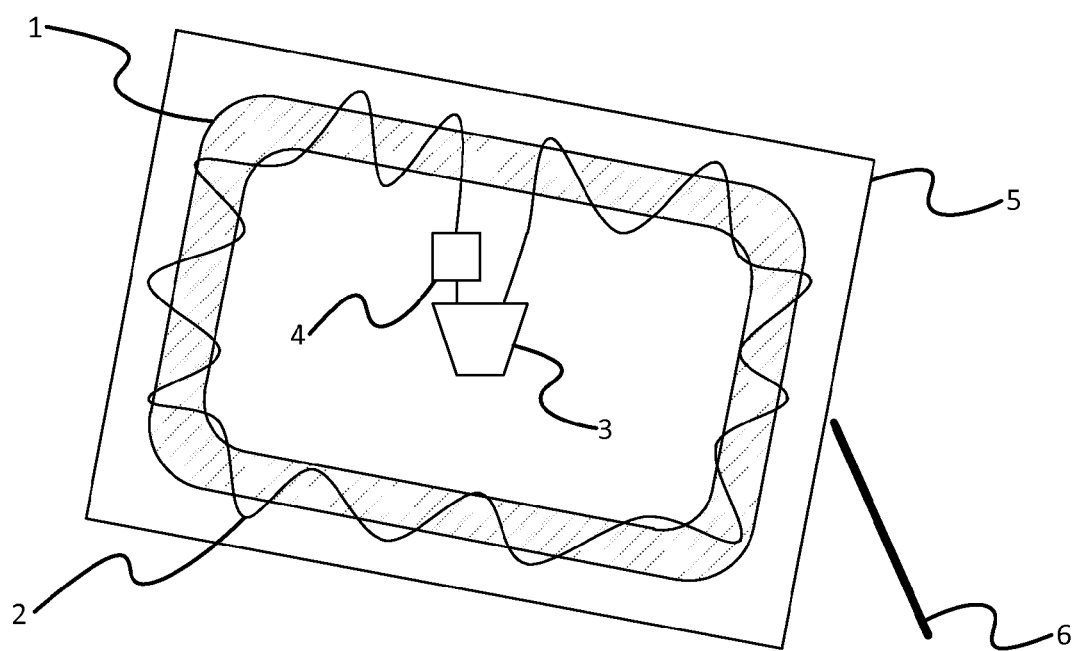
FIG. 2 shows an embodiment of the Qi emitter tool with a rectangular iron core.
Figure 3:
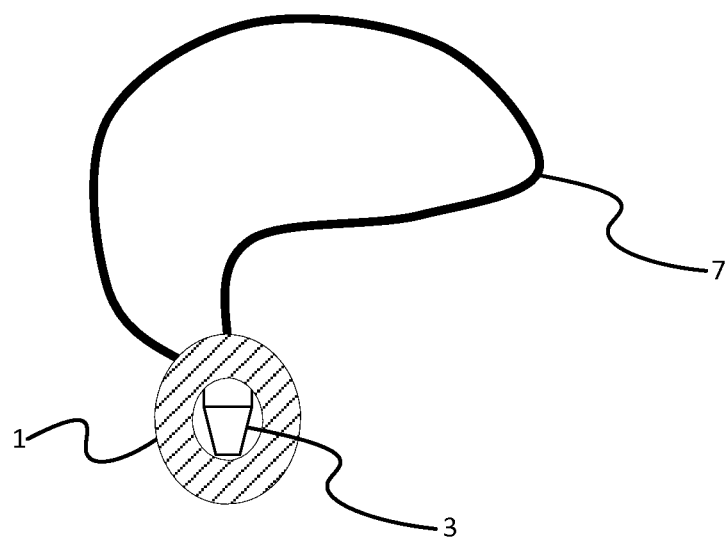
FIG. 3 shows an embodiment of the Qi emitter device in a necklace pendant style.

In FIG. 2, the iron core 1 is rectangular in shape, the Qi emission system is attached to a frame 5 and the frame is held up by a wire stand 6. In FIG. 3, the Qi emission device is made into a necklace pendant style. The necklace 7 may be worn around the neck.

During operation, the Qi emission device is placed a few feet from the user. The positioning is not critical. For example, the Qi emitting device can be stood on a table a few feet from the user who is sitting on a chair. The strong influence field from the Qi emitting device is sufficient to affect the whole body of the user no matter the exact positioning of the device. However, placing the Qi emitting device near a particular part of the body, for example, the chest, does add intensity of the Qi emission to that part of the body. The Qi emitting device is used to supplement Qi sessions from Qi practitioners. Often times, it is not practical to call upon a Qi practitioner, and the Qi emitting device can act as the substitute. Generally, sitting in the influence field of the Qi emitting device is similar to being in the influence of a Qi practitioner. Typically, the user feels his or her Qi circulation strengthen.

I claim:

1. A non-contact Qi emitting system consisting of a ferro-magnetic core with toroidal wire winding, wherein two ends of the winding are terminated at two leads of a piezo-crystal placed inside an opening of the core, and wherein the system is adapted to generate an influence field capable of affecting a person within the influence field.

2. The system of claim 1, wherein the ferro-magnetic core comprises iron.

3. The system of claim 1, wherein the piezo-crystal is a quartz crystal.

4. A non-contact Qi emitting system consisting of ferro-magnetic core with toroidal wire winding, wherein two ends of the winding are terminated at two leads of a piezo-crystal placed inside an opening of the core, wherein the core, winding and piezo-crystal are encased in an enclosure and held upright with a stand, and wherein the system is adapted to generate an influence field capable of affecting a person within the influence field.

5. The system of claim 4, wherein the enclosure comprises hard plastic.

6. The system of claim 4, wherein the stand comprise metal.

7. The system of claim 4 wherein the ferro-magnetic core comprises iron.

8. The system of claim 4 wherein the piezo-crystal is a quartz crystal.

9. A process adapted to provide Qi energy, the process comprising:
    coupling a ferro-magnetic core with toroidal wire winding to a piezo-crystal, wherein two ends of the winding are terminated at two leads of the piezo-crystal;
    placing the piezo-crystal inside an opening of the core; and
    placing the core and the piezo-crystal in proximity to a person.

\* \* \* \* \*